(12) United States Patent
Eiken

(10) Patent No.: US 10,966,639 B2
(45) Date of Patent: Apr. 6, 2021

(54) RESPIRATORY EFFORT BELT

(71) Applicant: Dymedix Diagnostics, Inc., Shoreview, MN (US)

(72) Inventor: Todd M. Eiken, Lindstrom, MN (US)

(73) Assignee: Dymedix Diagnostics, Inc., Shoreview, MN (US)

(*) Notice: Subject to any disclaimer, the term of this patent is extended or adjusted under 35 U.S.C. 154(b) by 656 days.

(21) Appl. No.: 15/456,949

(22) Filed: Mar. 13, 2017

(65) Prior Publication Data

US 2018/0256080 A1  Sep. 13, 2018

(51) Int. Cl.
*A61B 5/00* (2006.01)
*A61B 5/113* (2006.01)

(52) U.S. Cl.
CPC ..... *A61B 5/1135* (2013.01); *A61B 2560/0412* (2013.01)

(58) Field of Classification Search
None
See application file for complete search history.

(56) References Cited

U.S. PATENT DOCUMENTS

| | | | |
|---|---|---|---|
| 2008/0214078 A1* | 9/2008 | Vanmarcke | C09J 153/02 442/151 |
| 2008/0275356 A1* | 11/2008 | Stasz | A61B 5/0816 600/534 |

* cited by examiner

*Primary Examiner* — Rajeev P Siripurapu
*Assistant Examiner* — Sarah R Kingsley

(57) ABSTRACT

A respiratory effort belt to be worn by a person undergoing a sleep study comprises a PVDF piezo film transducer having opposite major surfaces metalized and electrical leads electronically connected to the metalized surfaces adhesively bonded to an inelastic cover layer that is, in turn, adhesively joined to an stretchable elastic band that functions as a belt to be secured to the person's chest or abdomen. The transducer produces a time-varying output voltage waveform due to rubbing contact between the elastic band and the PVDF film and not due to tensile forces acting on the film as the person's chest or abdomen rises and falls with inspiration and expiration.

5 Claims, 4 Drawing Sheets

RESPIRATORY EFFORT BELT

CROSS REFERENCE TO RELATED APPLICATIONS

None

STATEMENT OF GOVERNMENT INTEREST

None

BACKGROUND OF THE INVENTION

I. Field of the Invention

This invention relates generally to a respiratory sensing belt which incorporates a piezoelectric film as its sensing element, and more particularly to a unique respiratory sensing belt design in which a Polyvinylidine Fluoride (PVDF) film element produces an electrical output signal due to its rubbing contact with an elastic body-encircling band rather than to tensile stress acting on the PVDF transducer.

II. Discussion of the Prior Art

The closest prior art to the present invention is disclosed in published U.S. Patent Application Publication No. 2008/0275356 A1 which describes a respiratory sensing belt incorporating a piezo film transducer which is especially designed to be affixed to an elastic belt which, when fasten about the abdomen or chest of a subject, will produce an electrical signal output primarily due to tensile forces acting on the transducer as the belt is made to expand and to contract as the chest or abdomen rises and falls during a respiratory cycle.

As is explained in the afore referenced published application, a metalized strip of a PVDF polymer with a layer of metallization on opposed major surfaces is sandwiched between a label layer 22 and an elastic band 12 along with electrical leads 18 and 20 that have tabbed ends 24 and 26 in electrical contact with the metallization layers through conductive adhesive pads 16. In this design, the label layer 22 is designed to be "stretchable" and is adhesively affixed to the band 12. In this arrangement tensioning of the belt imparts a tensile or stretching force to the transducer element causing an electrical output to appear on the leads 18 and 20.

The present invention involves a modest change to the design described in the afore referenced published application, but one that is beneficial and non-obvious. It is beneficial in that it has been found to produce a more robust output signal varying with a wearer's respiratory cycle while lowering the manufacturing cost to a point where the respiratory belt can be disposed of after a single use, thereby obviating the need for cleaning and sterilization required by non-disposable articles of the type described.

SUMMARY OF THE INVENTION

The present invention provides a respiratory effort belt that comprises an elastic band of a length sufficient to encircle a person's torso and incorporating PVDF transducer consisting of a strip of PVDF film having a layer of metallization on opposed major surfaces of the strip. First and second electrical leads individually connect to the layers of metallization and completing the assembly is an inelastic cover layer adhesively bonded to the PVDF transducer. The inelastic cover layer has a greater area than that of the transducer, allowing the cover layer to be adhesively bonded onto the elastic band. An electrical output on the leads results primarily from rubbing contact between the elastic band and the PVDF transducer as the elastic band is stretched and relaxed rather than from tensile stress acting on the PVDF transducer as in the above described prior art. Comparative testing has been conducted between the performance of the respiratory effort belt of the prior art and that of the present invention. These testings have revealed that a larger output signal representative of a wearer's tidal breathing results from the use of the respiratory belt of the present invention.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
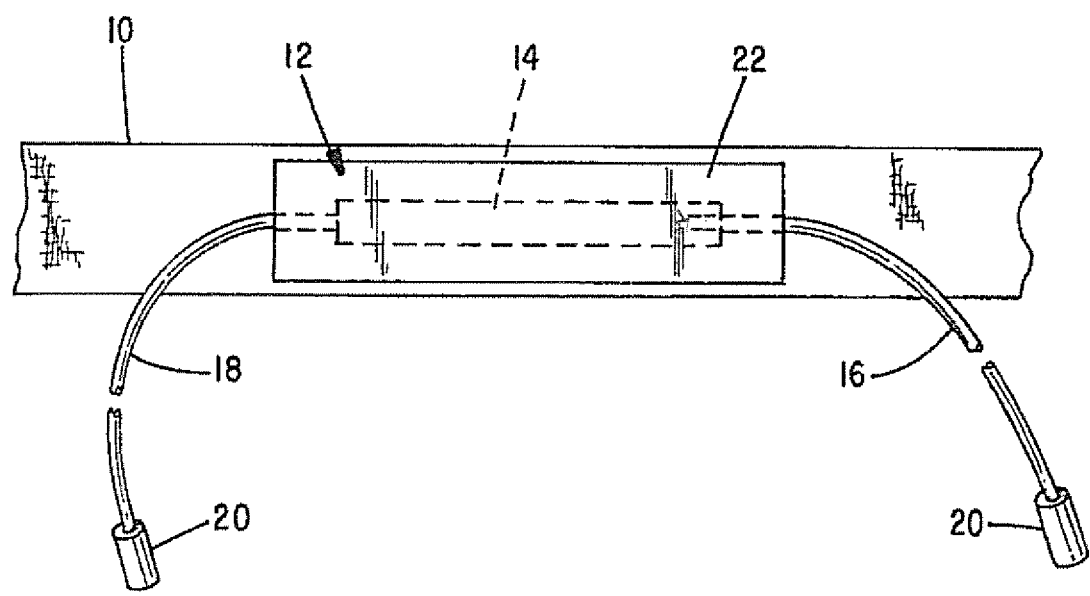
FIG. 1 is a top plan view of a segment of a body encircling band on which a transducer of the present invention is affixed.
Figure 2:
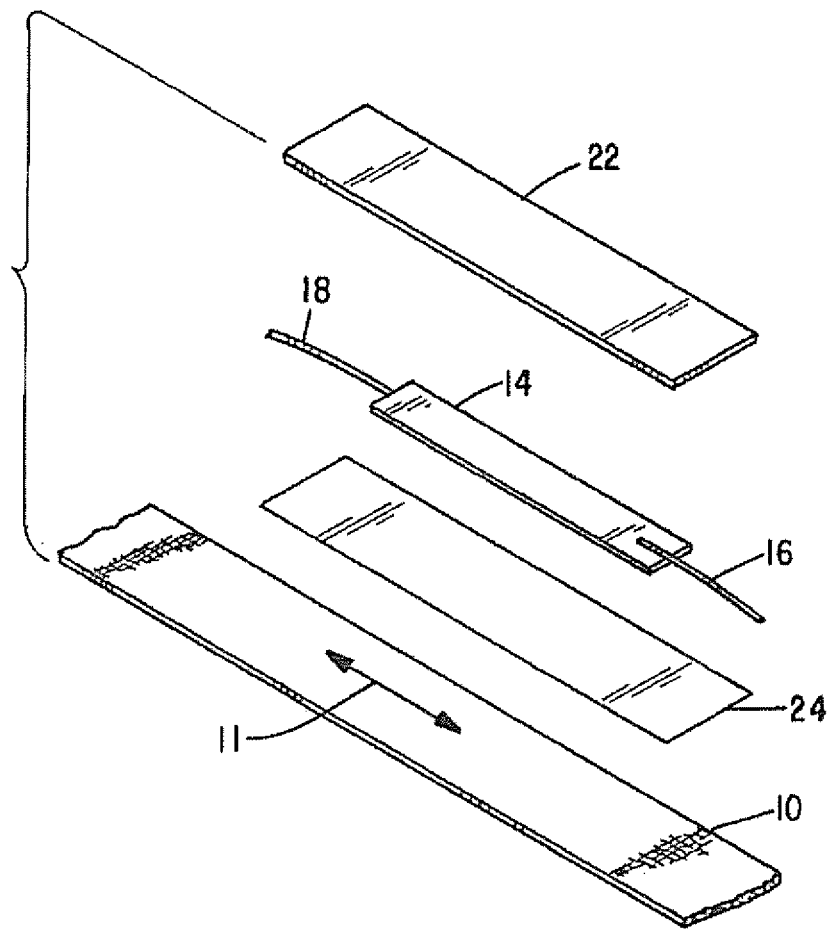
FIG. 2 is an exploded view of FIG. 1.

With reference to FIGS. 1 and 2 the respiratory effort belt of the present invention is seen to comprise a band of elastic fabric 10 whose length is sufficient to fit about the torso of a person undergoing a sleep study like a belt and that is longitudinally extendable and contractible along an axis indicated by arrow 11. While not shown in the drawings the band will have a suitable buckle, or Velcro® hook and loop clasp arrangement for joining the opposed ends of the band in surrounding relation to the person who is participating in the sleep study. Shown affixed to the band 10 in FIG. 1 is a transducer element 12 comprising a strip of a PVDF film having a thin coating of metallization on the opposed major surfaces thereof 14. Joined to the metallization layers are electrical leads 16 and 18 leading to electrical connectors 20 for mating the transducer to suitable signal processing circuits (not shown).

Figure 3:
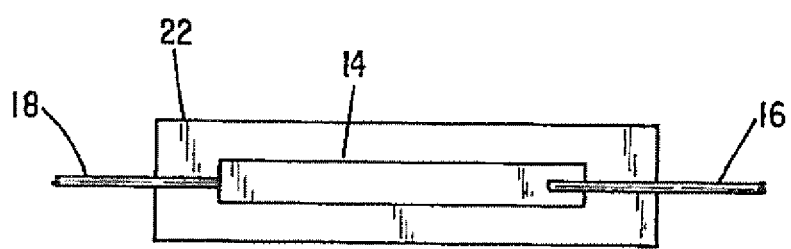
FIG. 3 is a plan view of the underside of the transducer element.

As seen in FIG. 3, the metalize strip of PVDF film 14 is first adhesively bonded to a cover layer 22. In accordance with the present invention, the cover layer 22 is a sheet of inelastic material rather than being elastic as in earlier described prior art designs. Without limitation, the inelastic cover layer 22 may be an ultra-smooth coated face-stock such as Fasson® Trans-Therm® 1C available from the Avery Dennison Corporation of Glendale, Calif., but limitation to that material is not intended. The recommended paper material exhibits a tensile strength of 28 pounds per inch width in the machine direction and 17 pounds per inch width in the cross direction which is more than adequate in restricting significant elongation of the PVDF film material when subject to tensile stress. The adhesive employed may be a general purpose not melt rubber based product such as Fasson® 246.

In that the PVDF transducer strip is adhesively bonded with the same adhesive to the cover sheet 22 the transducer's stretch or elongation is greatly restricted due to the limited ability of the cover sheet itself to stretch. The adhesive on the cover layer 22 and metalized PVDF strip 14 is protected, prior to use, by a sheet of Teflon coated release paper 24. At the time of use, the release paper layer 24 is peeled off the adhesive on cover layer 22 and the cover sheet 22, in turn, adhesively bonded to the elastic band 10 with the transducer strip 14 in intimate contact with the surface of the elastic band 10. Hence, when the elastic band is first stretched and then contracts, it rubs against the PVDF transducer strip 14 causing the piezo material to produce and enhanced voltage signal output on the leads 16 and 18 as compared to the signal that is obtained from prior art transducers whose output depends upon stretching and relaxation of the transducer element itself. Destructive testing has shown that the adhesive employed to secure the transducer 14 to the band 10 yields before the transducer 14 elongates.

Figure 4:
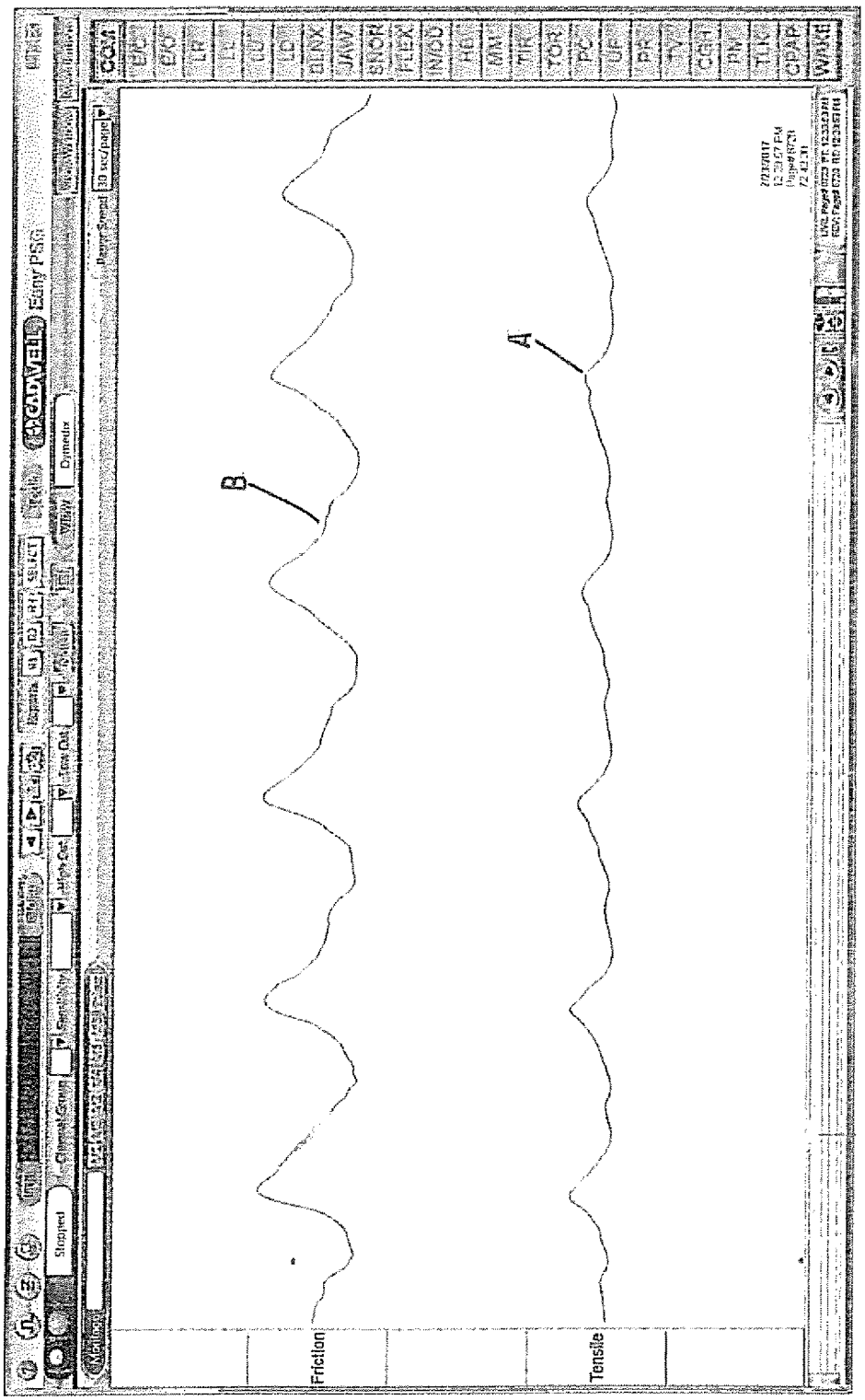
FIG. 4 shows a waveform labeled "A" derived from an effort belt of the prior art and a waveform labeled "B" derived from the effort belt of the present invention.

FIG. 4(A) illustrates the waveforms obtained from the effort belt of the prior art construction as taught by U.S. Patent Application Publication No. 2008/0275356A1 and FIG. 4(B) illustrates the waveform obtained from the effort belt of the present invention when the two are simultaneously being worn about the chest of a person undergoing normal tidal breathing. The amplitude difference is striking.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different materials and devices. For example, the transducer may have different sizes and shapes to accommodate a variety of belt sizes. Hence, it is clear that various modifications, both as to the equipment details, materials employed, and operating procedures can be accomplished without departing from the scope of the invention itself.

What is claimed is:

1. A respiratory effort belt comprising:
   (a) an elastic band of a length sufficient to encircle a person's torso;
   (b) a transducer comprising a strip of PVDF film having a layer of metallization on opposed major surfaces of the strip;
   (c) first and second electrical leads individually connected to the layers of metallization; and
   (d) an inelastic cover layer adhesively bonded to the transducer and having a greater area than that of the PVDF film, the cover layer being adhesively bonded onto the elastic band whereby an electrical output on said leads results primarily from rubbing contact between the elastic band and the PVDF film as the elastic band is stretched and contracts and not from tensile stress acting on the PVDF film.

2. The respiratory effort belt of claim 1 wherein the inelastic cover layer is a paper exhibiting a non-stretch characteristic when subjected to tensile forces transmitted to the cover layer from stretching of the elastic band.

3. The respiratory effort belt of claim 2 wherein the cover layer is a paper face-stock material.

4. The respiratory effort belt of claim 1 wherein the adhesive bonding the transducer cover layer is a hot melt rubber based adhesive.

5. The respiratory effort belt of claim 4 wherein the adhesive bonding the cover layer to the elastic band is a hot melt rubber based adhesive.

* * * * *